US009230534B2

(12) United States Patent
Xu

(10) Patent No.: US 9,230,534 B2
(45) Date of Patent: Jan. 5, 2016

(54) SUPPRESSION DEVICE FOR OUTDOOR NOISE IN INDOOR SPACE

(76) Inventor: Zhongyi Xu, Shenzhen (CN)

( * ) Notice: Subject to any disclaimer, the term of this patent is extended or adjusted under 35 U.S.C. 154(b) by 277 days.

(21) Appl. No.: 13/877,425

(22) PCT Filed: Oct. 18, 2011

(86) PCT No.: PCT/CN2011/001735
§ 371 (c)(1),
(2), (4) Date: Jul. 31, 2013

(87) PCT Pub. No.: WO2012/088745
PCT Pub. Date: Jul. 5, 2012

(65) Prior Publication Data
US 2013/0301843 A1 Nov. 14, 2013

(30) Foreign Application Priority Data
Dec. 29, 2010 (CN) ...................... 2010 2 0685129 U

(51) Int. Cl.
*A61F 11/06* (2006.01)
*G10K 11/175* (2006.01)
*G10K 11/178* (2006.01)

(52) U.S. Cl.
CPC .......... *G10K 11/175* (2013.01); *G10K 11/1788* (2013.01); *G10K 2210/3031* (2013.01); *G10K 2210/3214* (2013.01); *G10K 2210/3226* (2013.01)

(58) Field of Classification Search
USPC ........................................................ 381/71.1
See application file for complete search history.

(56) References Cited

U.S. PATENT DOCUMENTS 2,043,416 A 6/1936 Lueg
2006/0285697 A1* 12/2006 Nishikawa et al. .......... 381/71.1
(Continued)

FOREIGN PATENT DOCUMENTS

CN 87201016 2/1988
CN 101261829 9/2008
(Continued)

OTHER PUBLICATIONS

International Search Report and English translation of Written Opinion for PCT/CN2011/001735, mailed Feb. 16, 2012, 14 pages.
English translation of International Preliminary Report on Patentability for PCT/CN2011/001735, issued Jul. 2, 2013, 10 pages.

*Primary Examiner* — Sonia Gay
(74) *Attorney, Agent, or Firm* — Morrison & Foerster LLP

(57) ABSTRACT

The suppression device for outdoor noises in indoor space solves the technical problems on realizing better sound insulation effect within the room space and creating a quiet atmosphere for people's living environment. The structure includes an anti-noise sound source synchronized to and invert with outdoor noises. The circuit structure of suppression device includes a directional reception and processing circuit for outdoor noises, a attenuation control circuit, a multi-channel digital amplifier circuit, and loudspeaker being installed at the inlet of indoor noises. The directional reception and processing circuit for outdoor noises processes the noise signals collected from the outdoor environment and generates the inverted-phase signals, and then transmits them to the input terminal of attenuation control circuit. After being processed with attenuation by attenuation control circuit, the reverse-phase signals are sent out to input terminal of multi-channel digital amplifier circuit, which then enables the loudspeaker to generate noise compensation signals inverted to outdoor noises. This invention can provide the whole system with noise suppression capability over 28 dB.

8 Claims, 3 Drawing Sheets

(56) References Cited

U.S. PATENT DOCUMENTS

| | | | | |
|---|---|---|---|---|
| 2007/0180915 | A1* | 8/2007 | Goldberg et al. | 73/647 |
| 2007/0223714 | A1* | 9/2007 | Nishikawa | 381/71.1 |
| 2010/0150366 | A1* | 6/2010 | Davidson et al. | 381/71.1 |

FOREIGN PATENT DOCUMENTS

| | | |
|---|---|---|
| CN | 201177964 | 1/2009 |
| CN | 201943215 | 8/2011 |
| JP | 2008222094 | 9/2008 |

* cited by examiner

SUPPRESSION DEVICE FOR OUTDOOR NOISE IN INDOOR SPACE

CROSS-REFERENCE TO RELATED APPLICATIONS

This application is the national phase of PCT application PCT/CN2011/001735 having an international filing date of Oct. 18, 2011, which claims priority to Chinese Patent Application No. 201020685129.8, filed on Dec. 29, 2010. The contents of the above-listed applications are incorporated herein by this reference in their entireties.

FIELD OF THE INVENTION

This invention belongs to the field of technology on noise suppression, which involves in an outdoor noise cleaning system, particularly the relatively large environmental noise caused by outdoor construction. The noise cleaning system is designed for ensuring a quiet indoor space.

BACKGROUND OF THE INVENTION

The modernization of metropolitans has provided urban residents with convenience and enjoyment; however the accompanied noise pollution has brought inconvenience and damages to residents. Although the state has explicitly stipulated the noise level of general residences in cities, that is 55 dB shall not be exceeded in the daytime, and 45 dB shall not be exceeded at night. However, the noise interference of urban centers and residential buildings on both sides of busy roads always exceeds this specified limit. In order to improve the noise interference of residential buildings of these areas, first the vehicles on roads shall be restricted, and second the microenvironment noise within residential buildings shall be controlled. Obviously, it's impossible to restrict the vehicles on roads, therefore, we can only consider improving the environment within residential buildings. For the existing technology, we normally install acoustic insulation devices, such as double glass and seal treatment, which can suppress the relatively low outdoor noises but can not do much to suppress louder noises. Consequently, we need to consider seeking out a suppression method adapted to environmental noises, so as to meet residents' housing requirements.

It is well known that the sounds sent from the same sound source can be turned into two-way sounds with opposite phases and corresponding amplitudes after technical processing, which will then generate the "silence" when being played in the same space. This theory has been proposed on U.S. Pat. No. 2,043,416 of American patent as far back as 1934. Later on, the products of "silencer" and "pilot headset" etc. come out in 1940s and 1950s. The sound transmission space of these products is very small. In addition, in order to prevent the sounds from being reflected in this small space, and make the phases of two-way inverted-phase sounds change relatively, the periphery of this space were pasted with acoustic materials. These technical measures are fundamentally unable to be applied to an apartment with only dozens of square meters. Moreover, due to the various aesthetic tastes of individuals, the decoration materials can not be used as excellent acoustic materials. Therefore, the technology feasible in very small space is not practical in a larger space.

OBJECTS OF THE INVENTION

The purpose of this invention is to solve the technical problems on realizing better sound insulation effect within the room space and creating a quiet atmosphere for people's living environment. A suppression device for outdoor noises in indoor space is designed, which directionally receives the outdoor noises, collects the sound of outdoor noises, and transmits the sound signals with same noise amplitudes and opposite phases of outdoor noises, so as to compensate the outdoor noises with neutralization.

SUMMARY OF THE INVENTION

The technical solution adopted by this invention on realizing the invention purpose is that the structure of suppression device for outdoor noises in indoor space includes an anti-noise source that is the anti-phase synchronization of outdoor noises, the key factors are: the circuit structure of suppression device includes a directional reception and processing circuit for outdoor noises, a attenuation control circuit, a multi-channel digital amplifier circuit, and loudspeaker being installed at the inlet of noises, the directional reception and processing circuit for outdoor noise processes the noise signals collected from the outdoor environment and generates the inverted-phase signals, and then transmits them to the input terminal of attenuation control circuit, after being processed with attenuation by attenuation control circuit, the reverse-phase signals are sent out to input terminal of multi-channel digital amplifier circuit, which then enables the loudspeaker to generate noise compensation signals inverted to outdoor noises.

An ultra single directional sound sensing circuit composed by single directional microphone and ZY series chips is set at the incoming entrance of outdoor noises, it can receives the incoming noise signals from outdoor without being disturbed by indoor inherent noises, providing the sample for circuit system on cloning the incoming noise signals with anti phase and same amplitude.

Another ultra single directional sound sensing circuit composed by single directional microphone and ZY series chips is set indoors, which is placed near the flat plane speaker and points at the incoming direction of outdoor noises. The received sound signals are input into DSP system which generating the noise signals with anti phase and same amplitude, and automatically tracking and finely tuning the phase positions and amplitudes of output signals. Therefore, the frequency component distribution and corresponding energy of DSP system output signals are consistent with the incoming outdoor noises with opposite phase, we call this the "mirror image signals of outdoor noises".

There is one set of hi-fi stereo equipment in the system, which has low distortion of audio amplification, and adopts the single-direction panel loudspeaker. The "mirror image signals of outdoor noise" is sent through hi-fi stereo equipment to indoor space, with the direction same as incoming noise direction, and opposite to the direction of single-direction sampling microphone. The key component of sampling microphone is ZY series noise suppression chip, which can ensure that the isolation degree between single-direction sampling microphone and panel loudspeaker is over 23 dB.

For electrical signals of two-way sounds with same source or similar frequency component and equivalent energy, the use of differential synthesis in circuit will mutually eliminate and suppress the noises. The reason is that the transmission rate of electromagnetic wave is 300 thousand kilometers per second. Although two-way differential signals may encounter the transmission delay in each way, for the sound signals such delay can be neglected. However, for the sound waves transmitted in our living space, because transmission rate of mechanical sound wave is 344 meters per second, even the transmission distance of several centimeters can not be neglected. As the sampling microphone of system and loudspeaker playing the "mirror image signals of outdoor noise" can't be placed at the same point, and the placement location of loudspeaker is certain to be the side near room, thereby causing the noises played by loudspeaker "pull ahead" of actual incoming noises. The leading time is the ratio of effective placement distance between sampling microphone and loudspeaker and transmission speed of sound wave of 344 m/s. This delay can be processed when producing the "minor image signals of outdoor noise" by DSP digital processing technology.

Because the articles put in surrounding space and indoor walls, ceilings, and floors can generate the reflection of sound waves to cause the reverberation, the delay of this kind of reverberation containing reflected wave is hard to predict.

In other words, once the outdoor noises enter into the room, the reverberation will be formed by reflection of indoor walls, ceilings, and floors etc., therefore the outdoor noises are difficult to be suppressed. Consequently, the key technology of system is the single-direction outdoor noise sampling, and the single-direction playing of "minor image signals of outdoor noise" to the room by panel loudspeaker.

Because the incoming outdoor noises are in random state, the amount of the energy is impossible to be predicted. In addition to the requirements of high fidelity for sampling and playing, the requirements of energy self-adaptive circuit of system processing circuit are also extremely accurate. The precise analysis and calculation of sampling signals, including the judgment on whether to start the system through identifying incoming noises, are achieved through procedural programming design of DSP chips.

The beneficial effects of this invention is: select and use mature environmental noise suppression chips ZY1421, ZY 1623 and single-direction microphone to design the sound directional reception circuit, so as to ensure that the front and rear sensitivity of microphone is over 14 dB. Two sets of circuits respectively receive incoming noises from windows and the room, providing the whole system with noise suppression capability over 28 dB. The switch control modular circuit is set, evaluating indoor and outdoor noises. The compensation will start when it is quiet inside the room and highly noisy outside the room. The position of loudspeaker is set at the incoming entrance of outdoor noises, thereby effectively preventing the phase change caused by noise reflection of indoor walls.

From FIG. 2 to FIG. 7, R1-R42 are resistors, C1-C21 are capacitors, M is the microphone, SP1 and SP2 are loudspeakers, D1-D3 are diodes, Q1 is the file-effect tube, U8 is the noise suppression chip ZY 1421. The above integrated circuit has been commercially applied. U9 is the integrated circuit of interface ZY1623 for noise suppression chip, ZY 1421 and ZY1623 have obtained the patent (ZL201020233291.6), and has applied for the design of integrated circuit layout. U10 is the digital amplification chip, U1A, U1B, U2A, U3A, U7A, U7B are amplifiers, U4A, U4B and U4C are Schmitt triggers, USA is the NAND gate, and U6A and U6B are electronic switches.

DESCRIPTION OF PREFERRED EMBODIMENTS

Figure 1:
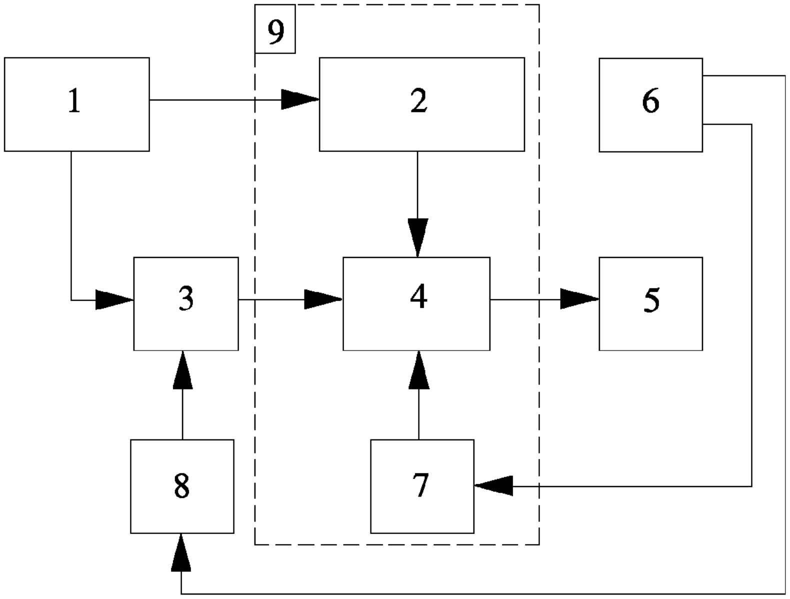
FIG. 1 Circuit Box of This invention
Figure 2:
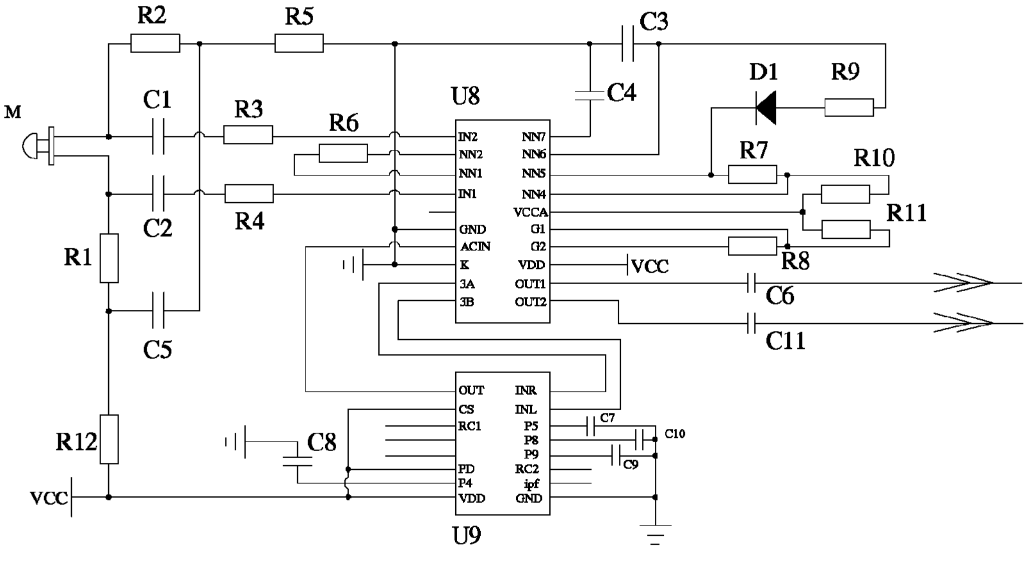
FIG. 2 Schematic Diagram Embodiment of Indoor Noise Reception Circuit or Outdoor Noise Reception Circuit FIG. 3 Schematic Diagram Embodiment of Indoor Noise Comparison Circuit or Outdoor Noise Comparison Circuit FIG. 4 Schematic Diagram of Attenuation Control Circuit FIG. 5 Schematic Diagram of Logic Switch Circuit FIG. 6 Schematic Diagram of Digital Amplification Circuit FIG. 7 Schematic Diagram of Indoor Noise Processing Circuit As shown in FIG. 1, 1 is the directional reception and processing circuit for outdoor noises, 2 is the outdoor noise assessment circuit, 3 is the attenuation control circuit, 4 is the logic switch circuit, 5 is the multi-channel digital amplifier circuit, 6 is the directional reception and processing circuit for indoor noises, 7 is the indoor noise assessment circuit, 8 is the square root detection circuit, and 9 is the switch control modular circuit.
Figure 3:
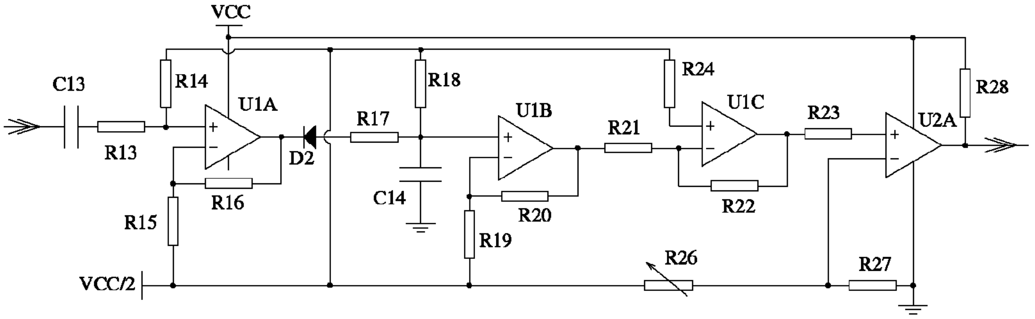
Figure 4:
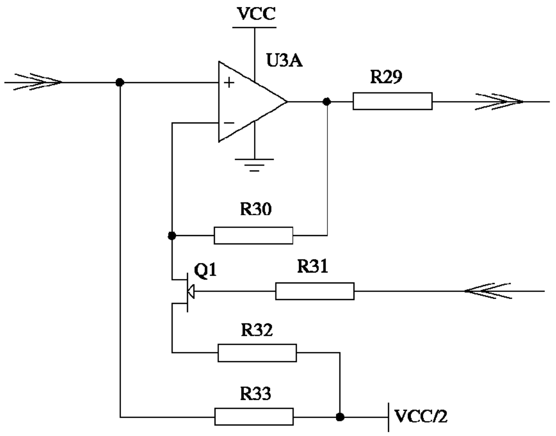
Figure 5:
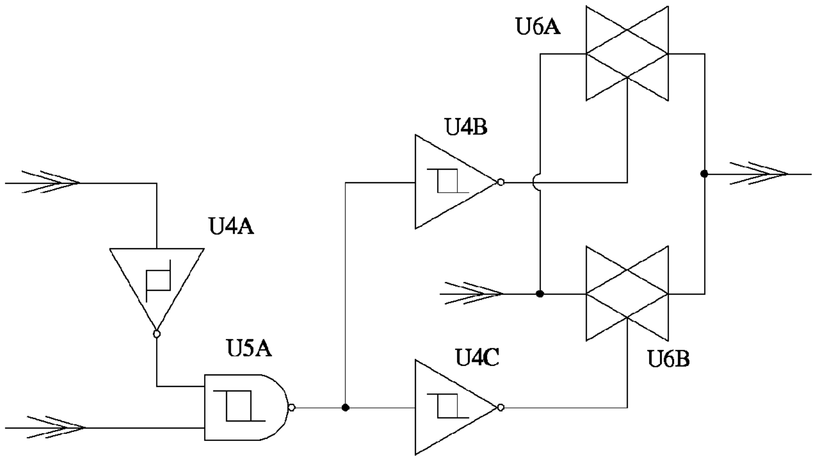
Figure 6:
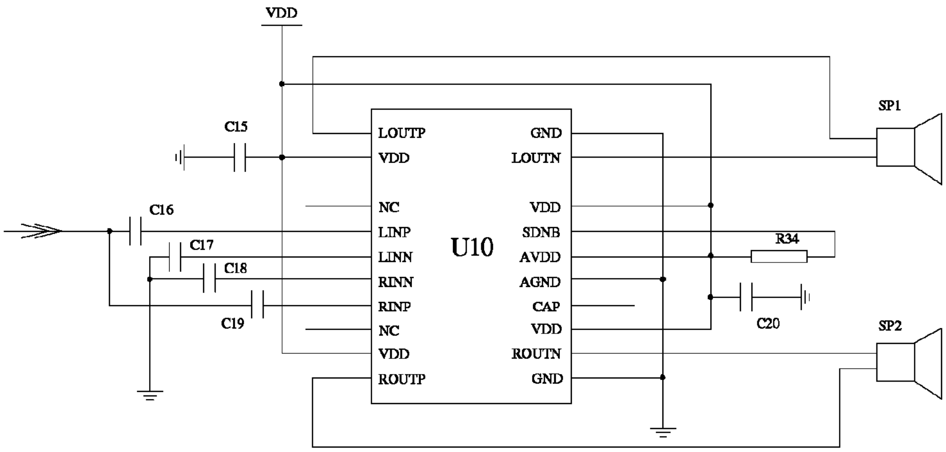
Figure 7:
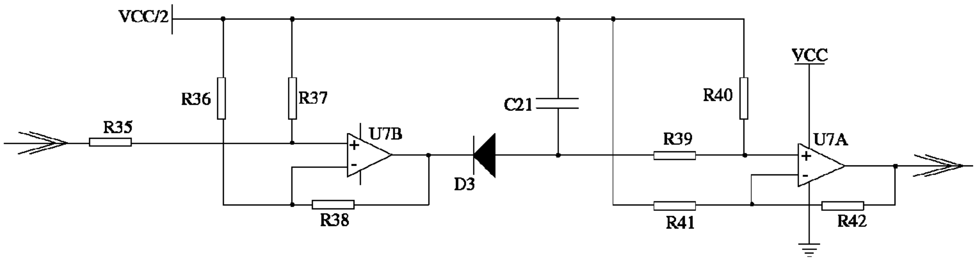

See FIG. 1, the structure of suppression device for outdoor noises in indoor space includes an anti-noise source that is the anti-phase synchronization of outdoor noises, the key factors are: the circuit structure of suppression device includes a directional reception and processing circuit for outdoor noises 1, a attenuation control circuit 3, a multi-channel digital amplifier circuit 5, and loudspeaker being installed at the inlet of indoor noises. The directional reception and processing circuit for outdoor noises 1 processes the noise signals collected from the outdoor environment and generates the inverted-phase signals, and then transmits them to the input terminal of attenuation control circuit 3. After being processed with attenuation by attenuation control circuit 3, the reverse-phase signals are sent out to input terminal of multi-channel digital amplifier circuit 5, which then enables the loudspeaker to generate noise compensation signals inverted to outdoor noises.

The principle of above circuit is that the directional reception and processing circuit for outdoor noises receives outdoor noises, which are processed into noise signals with opposite two-way phases, and then transmitted to noise suppression chip for noise suppression. After the inverted-phase signals are attenuated by attenuation control circuit, and sound signals with same noise amplitude and opposite phases of outdoor noise are transmitted, thereby conducting the noise compensation.

Because noises can be generated indoors, and the possible compensated and transmitted noises might be far higher than tolerance value of indoor environment, therefore, this invention has been further improved. The circuit structure of suppression device also includes a directional reception and processing circuit for indoor noises and a square-root detection circuit. The directional reception and processing circuit for indoor noises collects the noise signals of indoor environment and generates the inverted-phase noise signals, which is transmitted to the input terminal of square-root detection circuit. After being detected and amplified, the direct current pulse signals are sent to the controlled terminal of attenuation control circuit.

The principle of improvement is that the output value of inverted-phase compensation noise is controlled or adjusted according to the level of indoor noises, and then the indoor noises will be balanced.

This invention can be further improved by setting a switch control modular circuit, evaluating indoor and outdoor noises. The compensation will start when it is quiet inside the room and highly noisy outside the room. The plan is: here is a switch control modular circuit 9 between the attenuation control circuit 3 and multi-channel digital amplifier circuit 5, including an indoor noise assessment circuit 7, an outdoor noise assessment circuit 2 and a logic switch circuit 4. The indoor noise assessment circuit 7 and outdoor noise assessment circuit 2 respectively receive the in-phase signals sent from the directional reception and processing circuit for indoor noises 6 and directional reception and processing circuit for outdoor noises 1. After being compared and processed, the signals are transmitted to the input terminal of logic switch circuit 4. After being logically processed, the signals are transmitted to electronic switch by logic switch circuit 4.

See FIG. 2 to FIG. 7, the above-mentioned directional reception and processing circuit for indoor noises 6 has the same structure with directional reception and processing circuit for outdoor noises 1, including an indoor or outdoor microphone M, a balance input processing interface circuit and noise suppression chips U8, U9, and as supporting resistor-capacitor components. The sound signals collected by microphone M transmits two-path out-phase sound signals through phase-shift processing interface circuit, which will then be processed by noise suppression chips U8, U9 before sending out sound signals for noise suppression.

The above-mentioned attenuation control circuit 3 includes an amplifier U3A, a field effect tube Q1 and supporting resistors. The in-phase terminal of amplifier U3A receives the inverted-phase sound signals from directional reception and processing circuit for outdoor noises 1, with control signals received at the grid of field effect transistor Q1, the inverted-phase sound signals transmit the acoustic compensation signals after being regulated and gained.

The above-mentioned multi-channel digital amplifier circuit 5 consists of a number of digital amplifier circuits, and each digital amplifier circuit includes a digital amplifier chip U10 and peripheral supporting resistor-capacitor components. The signal input terminal of digital amplifier chip U10 receives the inverted-phase noise signals from attenuation control circuit 3 and then transmits to the two loudspeakers SP1, SP2 after being amplified.

The above-mentioned square-root detection circuit 8 includes a primary amplification circuit composed by an amplifier U7B and resistors, a detecting circuit composed by a diode D3 and capacitor C21, and a secondary amplification circuit composed by an amplifier U7A and supporting resistors. The in-phase terminal of amplifier U7B receives inverted-phase signals from the directional reception and processing circuit for indoor noises 6, and after the in-phase amplification, detection, and direct current amplification, the direct current pulse signals are transmitted to the input terminal of attenuation control circuit 3.

The above-mentioned indoor noise assessment circuit 7 is the same as the outdoor noise assessment circuit 2, including an amplification circuit composed by an amplifier U1A and supporting resistors and capacitors, a detection circuit composed by a diode D2, capacitors and resistors, a two-stage direct current amplification circuit composed by an amplifier U1B, an amplifier UIC and supporting resistors, as well as a voltage comparison circuit composed by an amplifier U2A and supporting resistors. The indoor noise assessment circuit 7 and outdoor noise assessment circuit 2 respectively receive the in-phase signals transmitted by directional reception and processing circuit for indoor noises 6 and directional reception and processing circuit for outdoor noises 1, and after the amplification, detection, re-amplification, and comparative processing, the voltage signals are transmitted to the input terminal of logic switch circuit 4.

The above-mentioned logic switch circuit 4 includes a NAND gate U5A, two electronic switches U6A, U6B, and three supporting triggers U4A, U4B, U4C. The NAND gate U5A receives the comparison signals from indoor noise assessment circuit 7 and outdoor noise assessment circuit 2, and after being processed, the control signals are transmitted to the two electronic switches U6A, U6B.

The above-mentioned loudspeaker is rectangular panel loudspeaker.

During the specific implementation of this invention, microphones are respectively set indoors and outdoors, and the panel loudspeaker is set at the indoor entrance of incoming noises, the directional reception and processing circuit for indoor noise 6 and directional reception and processing circuit for outdoor noises 1 receive noise signals in real time. The indoor noise assessment circuit 7 and outdoor noise assessment circuit 2 evaluate noises, when the indoor noises are relatively low and outdoor noises are relatively high, the electronic switches U6A and U6B can be started to transmit noise compensation signals. If the indoor noises are relatively high, such as talking, meeting or entertainment, then it's no need to conduct noise suppression. For specific comparison, the standard noise can be artificially set as required, thereby making the whole system more rational.

What is claimed is:

1. A suppression device for outdoor noises in indoor space includes an anti-noise source that is an anti-phase synchronization of outdoor noises, comprising:

a directional reception and processing circuit for outdoor noises, an attenuation control circuit, a multi-channel digital amplifier circuit, a loudspeaker being installed at the inlet of noises, a directional reception and processing circuit for indoor noises, a square-root detection circuit, and a switch control modular circuit between the attenuation control circuit and the multi-channel digital amplifier circuit, including an indoor noise assessment circuit, an outdoor noise assessment circuit and a logic switch circuit, wherein the directional reception and processing circuit for outdoor noises processes noise signals collected from the outdoor environment and generates inverted-phase signals, and then transmits them to the input terminal of the attenuation control circuit, after being processed with attenuation by the attenuation control circuit, reverse-phase signals are sent out to input terminal of the multi-channel digital amplifier circuit, which then enables the loudspeaker to generate noise compensation signals inverted-phase to outdoor noises, wherein the directional reception and processing circuit for indoor noises collects the noise signals of indoor environment and generates inverted-phase noise signals, which are transmitted to the input terminal of the square-root detection circuit, after being detected and amplified, direct current pulse signals are sent to the controlled terminal of the attenuation control circuit, and wherein the indoor noise assessment circuit and the outdoor noise assessment circuit respectively receive the in-phase signals sent from the directional reception and processing circuit for indoor noises and directional reception and processing circuit for outdoor noises, after being compared and processed, the signals are transmitted to the input terminal of the logic switch circuit, after being logically processed by logic switch circuit, the control signals are transmitted to electronic switch.

2. The suppression device for outdoor noises in indoor space according to claim 1, wherein the directional reception and processing circuit for indoor noises has the same structure with directional reception and processing circuit for outdoor noises, including an indoor or outdoor microphone, a balance input processing interface circuit and noise suppression chips, and as supporting resistor-capacitor components, the sound signals collected by microphone transmits two-path out-phase sound signals through phase-shift processing interface circuit, which will then be processed by noise suppression chips before sending out sound signals for noise suppression.

3. The suppression device for outdoor noises in indoor space according to claim 1, wherein the attenuation control circuit includes an amplifier, a field effect tube and supporting resistors, the in-phase terminal of amplifier receives the inverted-phase sound signals from directional reception and processing circuit for outdoor noises, with control signals received at the gate of field effect tube, adjusts the gain and transmit the acoustic compensation signals.

4. The suppression device for outdoor noises in indoor space according to claim 1, wherein the multi-channel digital amplifier circuit consists of a number of digital amplifier circuits, and each digital amplifier circuit includes a digital amplifier chip and peripheral supporting resistor-capacitor components, the signal input terminal of digital amplifier chip receives the inverted-phase noise signals from attenuation control circuit and then transmits to the two loudspeakers after being amplified.

5. The suppression device for outdoor noises in indoor space according to claim 1, wherein the square-root detection circuit includes a primary amplification circuit composed by an amplifier and resistors, a detecting circuit composed by a diode and capacitor, and a secondary amplification circuit composed by an amplifier and supporting resistors, the in-phase terminal of amplifier receives inverted-phase signals from the directional reception and processing circuit for indoor noises, and after the in-phase amplification, detection, and direct current amplification, the direct current pulse signals are transmitted to the input terminal of attenuation control circuit.

6. The suppression device for outdoor noises in indoor space according to claim 1, wherein the indoor noise assessment circuit is the same as the outdoor noise assessment circuit, including an amplification circuit composed by an amplifier and supporting resistors and capacitors, a detection circuit composed by a diode, capacitors and resistors, a two-stage direct current amplification circuit composed by an amplifier, an amplifier and supporting resistors, as well as a voltage comparison circuit composed by an amplifier and supporting resistors. The indoor noise assessment circuit and outdoor noise assessment circuit respectively receive the in-phase signals transmitted by directional reception and processing circuit for indoor noises and directional reception and processing circuit for outdoor noises, and after the amplification, detection, re-amplification, and comparative processing, the voltage signals are transmitted to the input terminal of logic switch circuit.

7. The suppression device for outdoor noises in indoor space according to claim 1, wherein the logic switch circuit includes a NAND gate, two electronic switches, and three supporting triggers, the NAND gate receives the comparison signals from indoor noise assessment circuit and outdoor noise assessment circuit, and after being processed, the control signals are transmitted to the two electronic switches.

8. The suppression device for outdoor noises in indoor space according to claim 1, wherein the loudspeaker is rectangular panel loudspeaker.

* * * * *